United States Patent [19]

Panandiker et al.

[11] Patent Number: 5,431,842
[45] Date of Patent: Jul. 11, 1995

[54] LIQUID DETERGENTS WITH ORTHO-SUBSTITUTED PHENYLBORONIC ACIDS FOR INHIBITION OF PROTEOLYTIC ENZYME

[75] Inventors: Rajan K. Panandiker, West Chester; David W. Bjorkquist, Wyoming, both of Ohio

[73] Assignee: The Procter & Gamble Company, Cincinnati, Ohio

[21] Appl. No.: 149,171

[22] Filed: Nov. 5, 1993

[51] Int. Cl.$^6$ ............................................. C11D 3/386
[52] U.S. Cl. ................................ 252/135; 252/174.12; 252/DIG. 12; 252/173; 435/188; 435/264
[58] Field of Search .................. 252/174.41, DIG. 12, 252/173, 135; 435/188, 264

[56] References Cited

U.S. PATENT DOCUMENTS

| | | | |
|---|---|---|---|
| 3,912,595 | 10/1975 | Phillipp et al. | 195/66 R |
| 4,261,868 | 4/1981 | Hora et al. | 252/529 |
| 4,537,706 | 8/1985 | Severson, Jr. | 252/545 |
| 4,537,707 | 8/1985 | Severson, Jr. | 252/545 |
| 4,900,475 | 2/1990 | Ramachandran | 252/532 |
| 5,030,378 | 7/1991 | Venegas | 252/174.12 |
| 5,124,066 | 6/1992 | Russell | 252/174.12 |

FOREIGN PATENT DOCUMENTS

| | | |
|---|---|---|
| 2004303 | 11/1989 | Canada. |
| 0478050 | 4/1992 | European Pat. Off.. |
| 9219707 | 11/1992 | WIPO. |

OTHER PUBLICATIONS

Philipp, M. and Bender, M. L.; "Kinetics of subtilisin and thioisubtilisin"; *Molecular and Cellular Biochemistry*, 51, pp. 5—32 (1983).

Philipp and Maripuri; "Inhibition of Subtilisin by Substituted Arylboronic Acids," *FEBS Letters*, vol. 133, No. 1, (1981) pp. 36–38.

*Primary Examiner*—Paul Lieberman
*Assistant Examiner*—Kery A. Fries
*Attorney, Agent, or Firm*—Jerry J. Yetter

[57] ABSTRACT

Liquid laundry detergents containing a protease and at least one additional enzyme wherein the additional enzyme is protected from degradation by the protease during storage by the presence of certain ortho substituted phenylboronic acids.

8 Claims, No Drawings

LIQUID DETERGENTS WITH ORTHO-SUBSTITUTED PHENYLBORONIC ACIDS FOR INHIBITION OF PROTEOLYTIC ENZYME

FIELD OF THE INVENTION

The invention pertains to liquid laundry detergents containing a protease enzyme and at least one additional enzyme. The additional enzyme is protected from degradation by the protease during storage of the detergent by the presence of certain phenyl boronic acids.

BACKGROUND OF THE INVENTION

Protease-containing liquid detergent compositions are well known. A commonly encountered problem, particularly with heavy duty liquid laundry detergents, is the degradation by proteolytic enzyme of second (non-protease) enzymes in the composition, such as lipase, amylase and cellulase or combinations thereof. The performance of the second enzyme upon storage, and its stability in product are thus impaired by proteolytic enzyme.

Boronic acids are known to reversibly inhibit proteolytic enzyme activity. This inhibition is reversible upon dilution, as occurs when a laundry detergent containing the enzyme is dissolved in the preparation of laundry wash water.

The inhibition constant (Ki) is ordinarily used as a measure of capacity to inhibit enzyme activity, with a low Ki indicating a more potent inhibitor. However, it has been found that not all boronic acids are sufficiently effective inhibitors of proteolytic enzyme in liquid detergents, particularly heavy duty liquid laundry detergents, regardless of their Ki values. This is believed to be due to a base catalyzed decomposition of the boronic acid caused by the alkaline medium of a heavy duty liquid, with the extent and rate of the decomposition being dependent on the structure of the boronic acid molecule.

A discussion of the inhibition of one proteolytic enzyme, subtilisin, is provided in Philipp, M. and Bender, M. L., "Kinetics of Subtilisin and Thiolsubtilisin", Molecular & Cellular Biochemistry, vol. 51, pp. 5–32 (1983). Inhibition constants for boronic acids are provided therein, and boronic acids are cited as subtilisin inhibitors. Low Ki values are said to indicate more effective inhibitors.

One class of boronic acid, peptide alkylboronic acid, is discussed as an inhibitor of trypsin-like serine proteases such as thrombin, plasma kallikrein and plasmin, especially in pharmaceuticals, in European Patent Application 0 293 881, Kettner et al., published Dec. 7, 1988.

European Patent Application Ser. No. 90/870212, published Nov. 14, 1990 discloses liquid detergent compositions containing certain bacterial serine proteases and lipases.

U.S. Pat. No. 4,908,150, Hessel et al, issued Mar. 13, 1990 describes liquid detergent compositions containing lipolytic enzymes wherein the stability of the lipolytic enzyme is said to be improved by inclusion of particular nonionic ethylene glycol containing copolymers.

U.S. Pat. No. 4,566,985, Bruno et al, issued Jan. 28, 1986 describes liquid cleaning compositions containing a mixture of enzymes including a protease and second enzymes. The composition also contains an effective amount of benzamidine hydrohalide to inhibit the digestive effect of protease on the second enzymes. The inhibition effect is reversed upon dilution.

In European Application 0 376 705, Cardinali et al, published Jul. 4, 1990, liquid detergent compositions containing a mixture of lipolytic enzymes and proteolytic enzymes have been described. The storage stability of the lipolytic enzyme is said to be enhanced by the inclusion of a lower aliphatic alcohol and a salt of a lower carboxylic acid and a surfactant system which is predominantly nonionic.

In European Patent Application 0 381 262 Aronson et al, published Aug. 8, 1990, mixtures of proteolytic and lipolytic enzymes in a liquid medium have been disclosed. The stability of lipolytic enzyme is said to be improved by the addition of a stabilizing system comprising boron compound and a polyol which are capable of reacting, whereby the polyol has a first binding constant with the boron compound of at least 500 l/mole and a second binding constant of at least 1000 $l^2/mole^2$.

PCT Application WO 92/19707, published Oct. 30, 1992 discloses meta substituted boronic acids as reversible protease inhibitors in liquid laundry detergents. They are indicated as being superior to the para substituted isomers for this purpose.

The stability of several substituted phenylboronic acids is discussed by Kuivila et al. in Canadian Journal of Chemistry at 3081–3090 (1963).

SUMMARY OF THE INVENTION

The present invention relates to an alkaline liquid laundry detergent composition comprising:

a. from about 0.001 to 10 weight % of certain phenyl boronic acids having structures described hereinafter:

b. from about 0.0001 to 1.0 weight % of proteolytic enzyme;

c. a performance-enhancing amount of at least one detergent-compatible second enzyme; and d. from about 1 to 80 weight % of detersive surfactant.

e. a liquid medium f. sufficient alkaline material to provide said composition with a pH of greater than 7 when measured as a 10% aqueous solution.

DESCRIPTION OF THE INVENTION

The instant liquid detergent compositions contain five essential ingredients: (a) certain phenyl boronic acids, (b) proteolytic enzyme, (c) detergent-compatible second enzyme, (d) detersive surfactant, (e) a liquid medium, and (f) sufficient alkaline material to provide the composition with a pH of greater than 7 when measured as a 10% solution in water. All percentages and proportions herein are "by weight" unless specified otherwise.

(a) o-Substituted Phenylboronic Acids

The boronic acids comprising component (a) of the composition of the present invention are ortho-substituted phenylboronic acids which have the following formulas: (1)

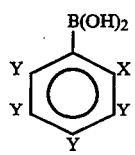

(1)

where X is —NO$_2$, —NH$_2$, —NHR, —OH, —OR,

or —NHSO$_2$R, wherein R is C$_1$–C$_4$ (preferably C$_1$–C$_2$) alkyl or aryl, and wherein each Y is H, C$_1$–C$_4$ (preferably C$_1$–C$_2$)alkyl or halogen (e.g., chloro- or bromo).

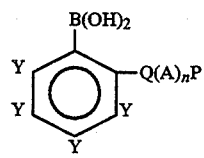

(2)

wherein Q is —O— or —NH, A is an amino acid moiety or a peptide moiety comprised of a combination of amino acid moieties, the amino acids being selected from alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenyalanine (Phe), proline (Pro), serine (Ser), threonine (Thr), tryptophan (Trp), tyrosine (Tyr) and valine (Vat), the said amino acid or peptide moiety being linked to Q as an ester or amide through the carboxylic acid of said amino acid or peptide at the C terminus, P is hydrogen or an amine protecting group, n is 1–5, and each Y is H, C$_1$–C$_4$ alkyl or halogen. Preferred amino acids are alanine, leucine, valine, isoleucine, proline, phenylalanine, tryptophan, glycine, arginine, and methionine. Amine protecting groups are groups which are attached to the amine end of an amino acid or peptide to block reaction by the amine when the carboxylic acid group is being reacted with another material. Typical amine protecting groups are methoxycarbonyl, benzyloxycarbonyl and tertiarybutoxycarbonyl.

Y is preferably H in both Type 1) and Type 2) compounds. The preferred compounds are those of Type (1) wherein X is

and the compounds of Type 2 wherein Q is —NH. It is believed that the compounds of Type (1) wherein X is —NHR,

—NHSO$_2$R and

wherein R is aryl, or C$_1$ to C$_3$ alkyl, and the compounds of Type 2 are novel.

It is believed that boronic acids inhibit proteolytic enzyme activity by forming a reversible covalent bond to the serine hydroxyl group in the active site of the proteolytic enzyme. Upon dilution, under typical wash conditions, protease activity is regained once this bond is broken and the boronic acid diffuses away from the proteolytic enzyme.

Aside from the ability to bond with protease, the efficacy of a protease inhibitor is also determined by the inherent chemical stability of the inhibitor in the medium in which it is used.

The ortho substituted phenylboronic acids of the present invention are superior to the comparable meta and para substituted compounds. This is believed to be due to (1) their better chemical stability in a concentrated alkaline detergent medium, and/or (2) their higher binding affinity to the protease.

Examples of boronic acids of the present invention are: o-hydroxyphenylboronic acid, o-nitrophenylboronic acid, o-aminophenylboronic acid, o-N-acetylaminophenylboronic acid, Moc-Phe-Gly-Ala-o-aminophenylboronic acid, o-N-sulfonamidophenylboronic acid, 2-amino-4-chlorophenylboronic acid, 2-nitro-3-ethylphenylboronic acid, Z-Gly-Ala-o- aminophenylboronic acid. In the above-recited peptide derivatives, the term "Moc" means methoxycarbonyl and the term Z means benzyloxycarbonyl, both of which are amine protecting groups. The peptide derivatives without the amine protecting groups are also useful in the present invention.

The ortho substituted boronic acids can conveniently be made, starting with the process described by Seaman et at., *J. Am. Chem. Soc.*, Vol. 53, p. 711 (Feb. 1931), incorporated herein by reference. The process involves preparation of o-nitro phenylboronic acid by reaction of fuming nitric acid with phenylboronic acid in the presence of acetic anhydride. The product is a mixture of approximately 95% ortho and 5% para nitro phenylboronic acid. The ortho and para isomers can be separated by crystallization. The o-nitro compound, which itself is useful in the present invention, can be converted to other derivatives by known reaction means. For example, the corresponding amino derivative can be prepared by catalytic hydrogenation of the nitro compound.

The hydroxyl derivative can be prepared by diazotization of the o-amino derivative, followed by hydrolysis. The ether and ester derivatives can be prepared by known reactions from the hydroxyl derivative, e.g., reaction with an alkyl chloride to form the ether and with a carboxylic acid to form the ester.

The amido derivative can be prepared by reacting the o-amino derivative with acetic anhydride.

The peptide derivative can be prepared by reacting the o-amino derivative with ethyleneglycol to produce the cyclic boronic ester, reacting the o-amino group with the desired peptide and then hydrolyzing the boronic ester back to the acid form.

The sulfonamido derivative can be prepared by reacting the o-amino derivative with an alkyl sulfonyl chloride.

In the present liquid detergent compositions, from about 0.001 to 10%, preferably about 0.02 to 5%, most preferably 0.05 to 2% of the ortho substituted phenylboronic acid is used.

(b) Proteolytic Enzyme

A second essential ingredient in the present liquid detergent compositions is from about 0.0001 to 1.0%, preferably about 0.0005 to 0.5%, most preferably about 0.002 to 0.1%, of proteolytic enzyme. Mixtures of proteolytic enzymes are also included within the term proteolytic enzyme herein. The proteolytic enzyme can be of animal, vegetable or microorganism (preferred) origin. More preferred is serine proteolytic enzyme of bacterial origin. Purified or nonpurified forms of the enzyme may be used. Proteolytic enzymes produced by chemically or genetically modified mutants are included by definition, as are close structural enzyme variants. Particularly preferred is bacterial serine proteolytic enzyme obtained from *Bacillus subtilis* and/or *Bacillus licheniformis*.

Suitable proteolytic enzymes include Alcalase®, Esperase®, Savinase®, all available from NOVO Nordisk N/A; Maxatase®, Maxacal®, and Maxapem 15® (protein engineered Maxacal®)), all available from Gist Brocades, and subtilisin BPN and BPN', available from Sigma Chemical Company. Preferred proteolytic enzymes are also modified bacterial serine proteases, such as those described in European Patent Application 251,446, Wells et al., published Jan. 7, 1988, and which is called herein "Protease B", and in U.S. Pat. No. 5,030,378, Venegas, issued Jul. 9, 1991, which refers to a modified bacterial serine proteolytic enzyme which is called "Protease A" herein. Preferred proteolytic enzymes are selected from the group consisting of Savinase®, Maxacal®, BPN', Protease A and Protease B, and mixtures thereof. Another preferred protease is that described in the U.S. Patent Application of A. Baeck, C. K. Ghosh, P. P. Greycar, R. R. Bott and L. J. Wilson entitled "Protease Containing Cleaning Compositions," and having U.S. Ser. No. 08/136,797 (P&G Case 5040), filed Oct. 14, 1993. This application is also incorporated by reference herein.

(c) Second Enzyme

The third essential ingredient in the present liquid compositions is a performance-enhancing amount of a detergent-compatible second enzyme. By "performance enhancing" is meant improving the enzyme-based cleaning performance of the composition beyond that achieved by use of the protease. By "detergent-compatible" is meant compatibility with the other ingredients of a liquid detergent composition, such as detersive surfactant, detergency builder, and alkaline pH. These second enzymes are preferably selected from the group consisting of lipase, amylase, cellulase, and mixtures thereof. The term "second enzyme" excludes the proteolytic enzymes discussed above, so each composition herein contains at least two kinds of enzyme, including at least one proteolytic enzyme and at least one additional enzyme which is not a protease.

The amount of second enzyme used in the composition varies according to the type of enzyme and the use intended. In general, from about 0.0001 to 1.0%, more preferably 0.001 to 0.5% on an active basis of these second enzymes are preferably used.

Mixtures of enzymes from the same class (e.g. lipase) or two or more classes (e.g. cellulase and lipase) may be used. Purified or non-purified forms of the enzyme may be used.

Lipase and cellulases are particularly preferred as second enzymes herein.

Any lipase suitable for use in a liquid detergent composition can be used herein. Suitable lipases for use herein include those of bacterial and fungal origin. Lipases from chemically or genetically modified mutants are included.

Suitable bacterial lipases include those produced by Pseudomonas, such as *Pseudomonas stutzeri* ATCC 19.154, as disclosed in British Patent 1,372,034, incorporated herein by reference. Suitable lipases include those which show a positive immunological cross-reaction with the antibody of the lipase produced by the microorganism *Pseudomonas fluorescens* IAM 1057. This lipase and a method for its purification have been described in Japanese Patent Application 53-20487, laid open on Feb. 24, 1978, which is incorporated herein by reference. This lipase is available under the trade name Lipase P "Amano," hereinafter referred to as "Amano-P" from Toyo Jozo Co., Togata Japan. Such lipases should show a positive immunological cross reaction with the Amano-P antibody, using the standard and well-known immunodiffusion procedure according to Ouchterlony (Acta. Med. Scan., 133, pages 76–79 (1950)). These lipases, and a method for their immunological cross-reaction with Amano-P, are also described in U.S. Pat. No. 4,707,291, Thom et al., issued Nov. 17, 1987, incorporated herein by reference. Typical examples thereof are the Amano-P lipase, the lipase ex *Pseudomonas fragi* FERM P 1339 (available under the trade name Amano-B), lipase ex *Psuedoomonas nitroreducens* var. *lipolyticum* FERM P 1338 (available under the trade name Amano-CES), lipases ex *Chromobacter viscosum*, e.g. *Chromobacter viscosum* var. *lipolyticum* NRRLB 3673, and further *Chromobacter viscosum* lipases, and lipases ex *Pseudomonas gladioli*. Other lipases of interest are Amano AKG and Bacillis Sp lipase (e.g., Solvay enzymes).

Other lipases which are of interest where they are detergent-compatible are those described in U.S. Pat. No. 5,223,169, El-Sayed et al., issued Jun. 29, 1993, EP A O 385 401, published Sep. 5, 1990, U.S. Pat. No. 5,153,135, Farin et al., issued Oct. 6, 1992, and U.S. Pat. No. 5,078,898, Jars, issued Jan. 7, 1992, all incorporated herein by reference.

Suitable fungal lipases include those producible by *Humicola lanuginosa* and *Thermomyces lanuginosus*. Most preferred is lipase obtained by cloning the gene from *Humicola lanuginosa* and expressing the gene in *Aspergillus oryzae* as described in European Patent Application 0 258 068, incorporated herein by reference, commercially available under the trade name Lipolase®.

From about 2 to 20,000, preferably about 10 to 6,000, lipase units of lipase per gram (LU/g) of product are typically used in these compositions. A lipase unit is that amount of lipase which produces 1 mmol of titratable butyric acid per minute in a pH stat, where pH is 7.0, temperature is 30° C., and substrate is an emulsion of tributyrin and gum arabic, in the presence of $Ca^{2+}$ and NaCl in phosphate buffer.

Any cellulase suitable for use in a liquid detergent composition can be used in these compositions. Suitable cellulase enzymes for use herein include those of bacterial and fungal origins. Preferably, they will have a pH optimum of between 5 and 9.5. From about 0.0001 to 1.0, preferably 0.001 to 0.5% on an active enzyme basis of cellulase can be used.

Suitable cellulases are disclosed in U.S. Pat. No. 4,435,307, Barbesgaard et al., issued Mar. 6, 1984, incorporated herein by reference, which discloses fungal cellulase produced from *Humicola insolens*. Suitable cellulases are also disclosed in GB-A-2,095,275 and U.S.

Pat. No. 3,844,890, Horikoshi et al., issued Oct. 29, 1974.

Examples of such cellulases are cellulases produced by a strain of Humicola insolens (Humicola grisea var. thermoidea), particularly the Humicola strain DSM 1800, and cellulases produced by a fungus of Bacillus N or a cellulase 212-producing fungus belonging to the genus Aeromonas, and cellulase extracted from the hepatopancreas of a marine mollusc (Dolabella Auricula Solander).

Any amylase suitable for use in a liquid detergent composition can be used in these compositions. Amylases include, for example, a-amylases obtained from a special strain of B.licheniforms, described in more detail in British Patent Specification No. 1,296,839. Amylolytic proteins include, for example, Rapidase TM, and Termamyl TM available from NOVO Nordisk and Maxamyl, available from Gist Brocades.

From about 0.0001% to 1.0, preferably 0.0005 to 0.5% on an active enzyme basis of amylase will typically be used.

(d) Detersive Surfactant

From about 1% to 80%, preferably about 3% to 50%, most preferably about 10% to 30%, of surfactant is an essential ingredient in detergent compositions of the present invention. The surfactant can be selected from the group consisting of anionics, nonionics, cationics, ampholytics, zwitterionics, and mixtures thereof. Anionic and nonionic surfactants are preferred.

Alkyl sulfate surfactants, either primary or secondary, are a type of anionic surfactant of importance for use herein. Alkyl sulfates have the general formula ROSO$_3$M wherein R preferably is a C$_{10}$-C$_{24}$ hydrocarbyl, preferably a alkyl straight or branched chain or hydroxyalkyl having a C$_{10}$-C$_{20}$ alkyl component, more preferably a C$_{12}$-C$_{18}$ alkyl or hydroxyalkyl, and M is H or a cation, e.g., an alkali metal cation (e.g., sodium potassium, lithium), substituted or unsubstituted ammonium cations such as methyl-, dimethyl-, and trimethyl ammonium and quaternary ammonium cations, e.g., tetramethyl-ammonium and dimethyl piperdinium, and cations derived from alkanolamines such as ethanolamine, diethanolamine, triethanolamine, and mixtures thereof, and the like. Typically, alkyl chains of C$_{12-16}$ are preferred for lower wash temperatures (e.g., below about 50° C.) and C$_{16-18}$ alkyl chains are preferred for higher wash temperatures (e.g., about 50° C.).

Alkyl alkoxylated sulfate surfactants are another category of useful anionic surfactant. These surfactants are water soluble salts or acids typically of the for formula RO(A)$_m$SO$_3$M wherein R is an unsubstituted C$_{10}$-C$_{24}$ alkyl or hydroxyalkyl group having a C$_{10}$-C$_{24}$ alkyl component, preferably a C$_{12}$-C$_{20}$ alkyl or hydroxyalkyl, more preferably C$_{12}$-C$_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperdinium and cations derived from alkanolamines, e.g., monoethanolamine, diethanolamine, and triethanolamine, and mixtures thereof. Exemplary surfactants are C$_{12}$C$_{18}$ alkyl polyethoxylate (1.0) sulfate, C$_{12}$-C$_{18}$ alkyl polyethoxylate (2.25) sulfate, C$_{12}$-C$_{18}$ alkyl polyethoxylate (3.0) sulfate, and C$_{12}$-C$_{18}$ alkyl polyethoxylate (4.0) sulfate wherein M is conveniently selected from sodium and potassium.

Other anionic surfactants useful for detersive purposes can also be included in the compositions hereof. These can include salts (including, for example, sodium potassium, ammonium, and substituted ammonium salts such a mono-, di- and triethanolamine salts) of soap, C$_9$-C$_{20}$ linear alkylbenzenesulphonates, C$_8$-C$_{22}$ primary or secondary alkanesulphonates, C$_8$-C$_{24}$ olefinsulphonates, sulphonated polycarboxylic acids, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, monoesters of sulfosuccinate (especially saturated and unsaturated C$_{12}$-C$_{18}$ monoesters) diesters of sulfosuccinate (especially saturated and unsaturated C$_6$-C$_{14}$ diesters), N-acyl sarcosinates, sulfates of alkylpolysaccharides such as the sulfates of alkylpolyglucoside, branched primary alkyl sulfates, alkyl polyethoxy carboxylates such as those of the formula RO(CH$_2$CH$_2$O)$_k$CH$_2$COO—M$^+$ wherein R is a C$_8$-C$_{22}$ alkyl, k is an integer from 0 to 10, and M is a soluble salt-forming cation, and fatty acids esterified with esethionic acid and neutralized with sodium hydroxide. Further examples are given in *Surface Active Agents and Detergents* (Vol. I and II by Schwartz, Perry and Berth).

Nonionic surfactants such as block alkylene oxide condensate of C$_6$ to C$_{12}$ alkyl phenols, alkylene oxide condensates of C$_8$-C$_{22}$ alkanols and ethylene oxide/propylene oxide block polymers (Pluronic TM -BASF Corp.), as well as semi polar nonionics (e.g., amine oxides and phosphine oxides) can be used in the present compositions. An extensive disclosure of these types of surfactants is found in U.S. Pat. No. 3,929,678, Laughlin et al., issued Dec. 30, 1975, incorporated herein by reference.

Ampholytic and zwitterionic surfactants such as described in U.S. Pat. No. 3,929,678, supra can also be used in the compositions of the invention.

Cationic surfactants suitable for use in the compositions herein are described in U.S. Pat. No. 4,228,044 Cambre, issued Oct. 14, 1980, incorporated by reference herein.

Alkylpolysaccharides such as disclosed in U.S. Pat. No. 4,565,647 Lienado (incorporated by reference herein) can be used as surfactants in the compositions of the invention.

Polyhydroxy fatty acid amides can be used as surfactants herein.

These materials have the formula:

wherein: R$^1$ is H, C$_1$-C$_4$ hydrocarbyl, 2-hydroxy ethyl, 2-hydroxy propyl, or a mixture thereof, preferably C$_1$-C$_4$ alkyl, more preferably C$_1$ or C$_2$ alkyl, most preferably C$_1$ alkyl (i.e., methyl); and R$^2$ is a C$_5$-C$_{31}$ hydrocarbyl, preferably straight chain C$_7$-C$_{19}$ alkyl or alkenyl, more preferably straight chain C$_9$-C$_{17}$ alkyl or alkenyl, most preferably straight chain C$_{11}$-C$_{15}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2$(-CHOR')(CHOH)$—$CH_2OH$, and alkoxylated derivatives thereof, where n is an integer from 3 to 5, inclusive, and R' is H or a cyclic or aliphatic monosaccharide. Most preferred are glycityls wherein n is 4, particularly —$CH_2$—$(CHOH)_4$—$CH_2OH$.

In Formula (I), $R^1$ can be, for example, methyl, ethyl, propyl, isopropyl, butyl, 2-hydroxy ethyl, or 2-hydroxy propyl.

$R^2CO$—$N<$ can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

A particularly desirable surfactant of this type for use in the compositions herein is alkyl-N-methyl glucomide, a compound of the above formula wherein $R_2$ is alkyl (preferably $C_{11}$–$C_{13}$), R, is methyl and Z is 1-deoxyglucityl.

(e) Liquid Medium

The liquid medium of the compositions herein is typically water, but may be a an organic solvent which is miscible with water or a combination of one or more of such organic solvents and water. Examples of suitable water miscible organic solvents are ethanol, propanol, isopropanol, ethylene glycol, propylene glycol and glycerine. The liquid medium comprises at least 10%, typically from about 10% to 70%, preferably 20% to 60% and most preferably about 40% to 50% of the composition.

(f) Alkaline Material

The compositions herein are formulated to have an alkaline pH, i.e., a pH greater than 7 when measured as a 10% solution in water. Typically the pH will be between about 7.5 and 11, preferably from about 7.5 to 8.5. The desired pH can be achieved by use of buffers (e.g., sodium bicarbonate, disodium hydrogen phosphate), alkalis (e.g., sodium hydroxide), alkaline detergency builders (such as described below), and/or organic bases such as monoethanolamine as is well known to those skilled in the art.

(g) Optional Ingredients

The compositions herein can contain various optional ingredients. A preferred optional ingredient is a detergency builder. These materials are used at levels of from 1% to about 50%, preferably about 3% to 30%, more preferably about 5% to 20% in the composition herein. Inorganic as well as organic builders can be used.

Inorganic detergency builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. Borate builders, as well as builders containing borate-forming materials that can produce borate under detergent storage or wash conditions (hereinafter, collectively "borate builders"), can also be used. Preferably, non-borate builders are used in the compositions of the invention intended for use at wash conditions less than about 50° C., especially less than about 40° C.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck, incorporated herein by reference. However, other silicates may also be useful such as for example magnesium silicate, which can serve as a stabilizing agent for oxygen bleaches, and as a component of suds control systems.

Examples of carbonate builders are the alkaline earth and alkali metal carbonates, including sodium carbonate and sesquicarbonate and mixtures thereof.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$M_z(zAlO_2 \cdot ySiO_2)$$

wherein M is sodium, potassium, ammonium or substituted ammonium, z is from about 0.5 to about 2; and y is 1; this material having a magnesium ion exchange capacity of at least about 50 milligram equivalents of $CaCO_3$ hardness per gram of anhydrous aluminosilicate. Preferred aluminosilicates are zeolite builders which have the formula:

$$Na_z[(AlO_2)_z(SiO_2)_y] \cdot xH_2O$$

wherein z and y are integers of at least 6, the molar ratio of z to y is in the range from 1.0 to about 0.5, and x is an integer from about 15 to about 264.

Specific examples of polyphosphates are the alkali metal tripolyphosphates, sodium, potassium and ammonium pyrophosphate, sodium and potassium and ammonium pyrophosphate, sodium and potassium orthophosphate, sodium polymeta phosphate in which the degree of polymerization ranges from about 6 to about 21, and salts of phytic acid.

Organic detergent builders preferred for the purposes of the present invention include a wide variety of polycarboxylate compounds. As used herein, "polycarboxylate" refers to compounds having a plurality of carboxylate groups, preferably at least 3 carboxylates.

Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates. A number of ether polycarboxylates have been disclosed for use as detergent builders. Examples of useful ether poly-carboxylates include oxydisuccinate, as disclosed in Berg, U.S. Pat. No. 3,128,287, issued Apr. 7, 1964, and Lamberti et al., U.S. Pat. No. 3,635,830, issued Jan. 18, 1972, both of which are incorporated herein by reference.

A specific type of ether polycarboxylates useful as builders in the present invention also include those having the general formula:

wherein A is H or OH; B is H or —O—CH(COOX)—CH$_2$(COOX); and X is H or a salt-forming cation. For example, if in the above general formula A and B are both H, then the compound is oxydissuccinic acid and its water-soluble salts. If A is OH and B is H, then the compound is tartrate monosuccinic acid (TMS) and its water-soluble salts. If A is H and B is —O—CH(COOX)—CH$_2$(COOX), then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80. These builders are disclosed in U.S. Pat. No. 4,663,071, issued to Bush et al., on May 5, 1987.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen).

Still other ether polycarboxylates include copolymers of maleic anhydride with ethylene or vinyl methyl ether, 1,3,5-trihydroxy benzene-2,4,6-trisulphonic acid, and carboxymethyloxysuccinic acid.

Organic polycarboxylate builders also include the various alkali metal, ammonium and substituted ammonium salts of polyacetic acids. Examples include the sodium, potassium, lithium, ammonium and substituted ammonium salts of ethylenediamine tetraacetic acid, and nitrilotriacetic acid.

Also included are polycarboxylates such as mellitic acid, succinic acid, oxydisuccinic acid, polymaleic acid, benzene 1,3,5-tricarboxylic acid, and carboxymethyloxysuccinic acid, and soluble salts thereof.

Citrate builders, e.g., citric acid and soluble salts thereof (particularly sodium salt), are suitable polycarboxylate builders for the compositions herein.

Other carboxylate builders include the carboxylated carbohydrates disclosed in U.S. Pat. No. 3,723,322, Diehl, issued Mar. 28, 1973, incorporated herein by reference.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference.

Useful succinic acid builders include the $C_5$–$C_{20}$ alkyl succinic acids and salts thereof. A particularly preferred compound of this type is dodecenyl-succinic acid. Alkyl succinic acids typically are of the general formula R—CH(COOH)CH$_2$(COOH) i.e., derivatives of succinic acid, wherein R is hydrocarbon, e.g., $C_{10}$–$C_{20}$ alkyl or alkenyl, preferably $C_{12}$–$C_{16}$ or wherein R may be substituted with hydroxyl, sulfo, sulfoxy or sulfone substituents, all as described in the above-mentioned patents.

The succinate builders are preferably used in the form of their water-soluble salts, including the sodium, potassium, ammonium and alkanolammonium salts.

Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Another type of useful builder consists of ethylenediamine disuccinic acid and the alkali metal and ammonium salts thereof. See U.S. Pat. No. 4,704,233, Hartman et al., incorporated herein by reference.

Examples of useful builders also include sodium and potassium carboxymethyloxymalonate, carboxymethyloxysuccinate, ciscyclohexanehexacarboxylate, ciscyclopentanetetracarboxylate, and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, and converted to the corresponding salt.

Polycarboxylate builders are also disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

A particularly desirable builder system for use herein is one comprising a mixture of a $C_{10}$–$C_{18}$ monocarboxylic acid and citric acid or a salt thereof. When using this system, the composition will preferably contain from about 1% to about 18% of the monocarboxylic acid and from about 0.2% to 10% of the citric acid or titrate salt.

Other optional ingredients for the compositions herein include soil release polymers, optical brighteners, hydrotropes, bleaches, bleach activators, suds control agents, antibacterial agents, and additional enzyme stabilizers, e.g., ethoxylated tetraethylene pentamine.

The invention will be illustrated by the following examples, which are not to be construed in any way as limitations on the invention.

EXAMPLE I

Preparation of o-aminophenylboronic Acid

To a three necked round bottom flask equipped with an addition funnel (and argon inlet), thermometer and septum is added phenylboronic acid (40.13 g, 0.33 moles). Acetic anhydride (400 ml) is charged through the septum via syringe. Using a stir bar the mixture is then stirred under argon until the temperature reaches 0° C. with external cooling (ice bath). Fuming nitric acid (25.01 g, 0.397 moles) is added slowly over the course of thirty minutes. The reaction is then allowed to stir an additional two hours at 0° C., before removing the ice bath and allowing the reaction to warm to room temperature. The reaction is poured into ice water (1 L) at which point it appears cloudy. After stirring overnight, however, it becomes homogeneous. The solution is paced on a rotary evaporator at 40° C. under a 5 mm vacuum. When the volume is reduced by about 50%, enough water is added to bring the volume back to 100%. This process is repeated twice more, before bringing the volume to about 300 ml on the rotary evaporator when a precipitate is noticed. Twenty hours are allowed for complete crystallization, and the solids (p-nitrobenzeneboronic acid, 3.66 g) are removed by filtration. Enough water is then added to the filtrate to bring the total volume to 800 mi. The volume is reduced once more under reduced pressure to about 150 ml when a precipitate begins to form. The solids (o-nitrophenylboronic acid, 48.04 g) are collected by filtration and dried in a vacuum oven. To a pressure vessel is added o-nitrophenylboronic acid (31.64 g), 10% palladium on carbon (6.3 g) and ethanol (100 ml). The vessel is shook at room temperature under 50 psi hydrogen on a PARR shaker. After four hours the catalyst is removed by filtration, and the filtrate taken to dryness under reduced pressure. The solids (o-aminophenylboronic acid, 24.4 g) are dried under vacuum for 18 hours.

EXAMPLE 2

Preparation of o-N-Acetylaminophenylboronic Acid

To a solution of o-aminophenylboronic acid (6.73 g, 49.1 mmoles) in dioxane (100 ml) is added acetic anhydride (25.1 g, 246 mmoles). The reaction is heated at 100° C. for 17 hours. After cooling, the reaction volatiles are removed under reduced pressure to leave a thick yellow gel, which after chromatography affords o-N-acetylaminophenylboronic acid (7.33 g).

EXAMPLE 3

Preparation of Z-Gly-Ala-o- Aminophenylboronic Acid

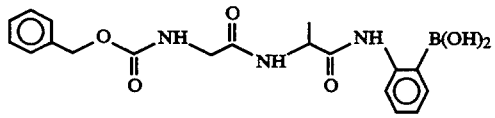

To a solution of o-aminophenylboronic acid (13.7 g, 100 mmoles) in dichloromethane (200 ml) is added ethylene glycol (6.30 g, 102 mmoles). The solution is shaken for 20 minutes, and then stirred over solid sodium sulfate. Removal of the volatiles affords ethylene o-aminophenylboronate. To a flame dried three neck round bottom flask equipped with septum, stopper and gas inlet, is added ethylene o-aminophenylboronate (0.36 g, 2.20 mmoles) in dry dimethylformamide (10 ml). To this solution is added Z-Gly-Ala (0.62 g, 2.21 mmoles), triethylamine (0.62 ml, 4.45 mmoles), and finally diethyl cyanophosphonate (0.37 ml, 2.44 mmoles). After stirring the reaction at room temperature for 17 hours, the DMF is removed under reduced pressure. The remaining residue is dissolved in ethyl acetate, and washed sequentially with 10% HCl, saturated sodium bicarbonate, and brine. After drying the organic phase over magnesium sulfate, the salts are removed by filtration and filtrate concentrated in vacuum to leave (0.63 g) of Z-Gly-Ala-o- aminophenylboronic acid. This compound can be used "as is" in the present invention, or the benzyloxycarbonyl (Z) group can be removed by hydrogenolysis (see first step of Example 4).

EXAMPLE 4

Preparation of Moc-Phe-Gly-Ala-o- Aminophenylboronic Acid

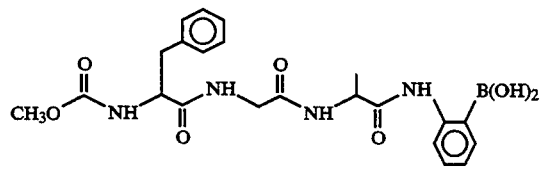

To a pressure vessel is added Z-Gly-Ala-o- aminophenylboronic acid, the compound of Example 3 (0.60 g, 1.5 mmoles), ethanol (20 ml), and 10% palladium on carbon (0.12 g). The vessel is shook under 50 psi hydrogen on a PARR apparatus for three hours at room temperature. The catalyst is removed by filtration and the solvent removed under reduced pressure to leave a paste, which was further dried in a vacuum oven to yield H-Gly-Ala-o aminophenylboronic acid (0.38 g). H-Gly-Ala-o- aminophenylboronic acid (0.354 g, 1.33 mmoles) is then stirred vigorously for thirty minutes in dichloromethane (20 ml) containing ethylene glycol (0.25 mi) and magnesium sulfate (2 g). The solution is filtered and the volatiles removed under reduced pressure. The residue is dissolved in dichloromethane and washed with cold water. After drying the organic phase over magnesium sulfate, the solvent is removed under reduced pressure to leave ethylene H-Gly-Ala-o-aminophenylboronate, which is added (0.302 g, 1.04 mmoles) to a flame dried three necked flask equipped with a stopper, septum, and gas inlet. While stirring under an argon atmosphere at room temperature, first MOC-Phe (0.232 g, 1.03 mmoles) dissolved in DMF (3 mi), and then triethylamine (0.29 mi, 2.08 mmoles) is added via a syringe. Lastly diethyl cyanophosphonate (0.17 ml, 1.12 mmoles) dissolved in DMF (7 ml) is added. After the reaction is stirred eighteen hours at room temperature, the DMF is removed under reduced pressure. After drying the organic phase with magnesium sulfate, the solids are removed by filtration and the filtrate concentrated under vacuum to leave Moc-Phe-Gly-Ala-o- aminophenylboronic acid (0.30 g). This material can be used "as is" in the present invention, or the methoxycarbonyl group (Moc) can be removed by hydrolysis.

EXAMPLE 5

A liquid laundry detergent of the present invention is prepared by mixing the following ingredients:

|  | WT % |
|---|---|
| C14–15 alkyl (ethoxy 2.25) sulfonic acid | 18.0 |
| C12–13 alkyl ethoxylate (9) | 2.0 |
| C12-N-methylglucamide | 5.0 |
| Citric acid | 4.0 |
| Ethanol | 3.5 |
| Monoethanolamine | 2.0 |
| 1,2 Propanediol | 7.0 |
| Sodium Formate | 0.6 |
| Boric acid | 2.0 |
| Tetraethylene pentamine ethoxylate (16) | 1.18 |
| Protease B(34 g/l) | 1.16 |
| Lipolase (100 K LU/g)* | 0.10 |
| Carezyme (5000 Cevu/g)** | 0.50 |
| Soil release Polymer | 0.15 |
| Silicone Suds suppresser | 0.10 |
| Brightener | 0.10 |
| o-Acetylaminophenylboronic acid | 0.20 |
| Water, NaOH*** and minors | Balance to 100% |

*A lipase from NOVO Nordisk N/A.
**A cellulase from NOVO Nordisk N/A.
***Sufficient NaOH is used to neutralize the acidic materials used in preparing the composition and to produce a pH of about 8 when the finished composition is dissolved in water at a concentration of 10%.

The composition is prepared according to the following procedure:

The alkyl polyethoxylate sulfonic acid is first mixed thoroughly with monoethanolamine, NaOH and alkyl polyethoxylate. Then, bode acid and citric acid are added slowly while the solution is being stirred rapidly to reach a pH around 8.0. The N-methyl glucamide, brightener, ethoxylated tetraethylene pentamine and soil release polymer are added. NaOH is used to finally adjust the pH to 8.0 at 10% concentration in water.

After the temperature is lowered, sodium formate, o-acetylaminophenylboronic acid, enzymes, and suds suppresser are added. Water is added finally to achieve the final target composition Ethanol and propylene glycol are present in the alkylpolyethoxylate sulfonic acid and N-methyl glucamide surfactants which are used in the composition.

Comparable compositions of the invention are prepared by substituting Moc-Phe-Gly-Ala-o- aminophenylboronic acid, o-aminophenylboronic acid, o-nitro-phenylboronic acid or Z-Gly-Ala-o- aminophenylboronic acid for o-acetylaminophenylboronic acid.

EXAMPLE 6

A liquid laundry detergent of the present invention is prepared by mixing the following ingredients, and using a preparation procedure substantially the same as in Example 5.

|  | WT % |
|---|---|
| C14–15 alkyl (ethoxy 2.25) sulfonic acid | 13.80 |
| C12–13 alkyl ethoxylate (9) | 2.22 |
| C12.3 Linear alkyl benzene sulfonic acid | 9.86 |
| Citric acid | 7.10 |
| Ethanol | 1.93 |
| Monoethanolamine | 0.71 |
| 1,2 Propanediol | 7.89 |
| Sodium cumene sulfonate | 1.80 |
| Sodium Formate | 0.08 |
| Sodium Hydroxide | 6.70 |
| Tetraethylene pentamine ethoxylate (16) | 1.18 |
| Protease B (34 g/l) | 1.16 |
| Lipolase (100 K LU/g)* | 0.90 |
| Soil release Polymer | 0.29 |
| Silicone Suds suppresser | 0.01 |
| Brightener | 0.10 |
| o-Acetylaminophenylboronic acid | 0.10 |
| Water and minors | Balance to 100% |

*A lipase from NOVO Nordisk N/A.

The composition has a pH (10% solution) in water of about 8.1.

What is claimed is:

1. An alkaline liquid laundry detergent composition comprising:
   a. from about 0.001 to 10 weight % of a phenyl boronic acid, or mixture of phenyl boronic acids, selected from the group consisting of:

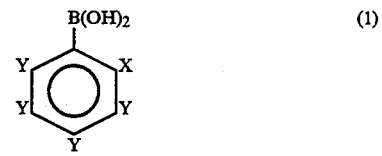

where X is selected from the group consisting of —NO2, —NHR, —OH, —OR,

or —NHSO2R, wherein R is C1–C4 alkyl or aryl, and wherein each Y is selected from the group consisting of H, C1–C4 alkyl and halogen, and

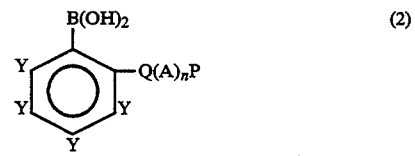

wherein Q is —O— or —NH, A is an amino acid moiety or a peptide moiety comprised of a combination of amino acid moieties, the amino acid being selected from the group consisting of Ala, Arg, Asn, Asp, Cys, Gln, Glu, Gly, His, Ile, Leu, Lys, Met, Phe, Pro, Ser, Thr, Trp, Tyr and Vat, the amino acid or peptide moiety being linked to Q as an ester or amide through the carboxylic acid at the C terminus, P is selected from the group consisting of hydrogen, and amine protecting groups, n is 1–5 and each Y is selected from the group consisting of hydrogen, C1–C4 alkyl and halogen.
   b. from about 0.0001 to 1.0 weight % of proteolytic enzyme;
   c. a performance-enhancing amount of at least one detergent-compatible second enzyme;
   d. from about 1 to 80 weight % of detersive surfactant;
   e. a liquid medium; and
   f. sufficient alkaline material to provide the composition with a pH of greater than 7 when measured as a 10% solution in water.

2. The composition of claim 1 wherein Component c. is selected from the group consisting of lipase, amylase, cellulase and mixtures thereof.

3. The composition of claim 2 wherein Component d. is selected from the group consisting of anionic and nonionic surfactants and mixtures thereof.

4. The composition of claim 3 wherein the pH of a 10% aqueous solution of said composition is from about 7.5 to 11.

5. The composition of claim 4 wherein each Y in Component a.(1) and a.(2) is hydrogen.

6. The composition of any one or more of claims 1 through 5 wherein X in Component a.(1) is

and wherein in Component a.(2), Q is —NH and P is selected from the group consisting of hydrogen, methoxycarbonyl, benzyloxycarbonyl and tertiarybutoxycarbonyl.

7. The composition of claim 6 wherein in Component a.(2) A is selected from the group consisting of Ala, Leu, Val, Ile, Pro, Phe, Trp, Gly, Arg and Met, and mixtures thereof.

8. The composition of claim 6 wherein in Component a.(2), A is selected from the group consisting of Ala, Gly and Phe and mixtures thereof.

* * * * *